United States Patent [19]

Peterson et al.

[11] Patent Number: 5,827,836
[45] Date of Patent: Oct. 27, 1998

[54] RETINOID GLYCEROL PHOSPHOLIPID CONJUGATES

[75] Inventors: Andrew C. Peterson; Thaddeus P. Pruss; Parvin T. Yazdi, all of Madison, Wis.

[73] Assignee: Clarion Pharmaceuticals Inc., Madison, Wis.

[21] Appl. No.: 749,512

[22] Filed: Nov. 15, 1996

Related U.S. Application Data

[60] Provisional application No. 60/009,546 Jan. 2, 1996.
[51] Int. Cl.$^6$ ............................... A61K 31/66; C07F 9/10
[52] U.S. Cl. .................................. 514/77; 554/80; 554/81
[58] Field of Search ................................... 514/77, 80, 81

[56] References Cited

U.S. PATENT DOCUMENTS

| | | |
|---|---|---|
| 4,372,949 | 2/1983 | Kodama et al. . |
| 5,116,992 | 5/1992 | Braquet et al. . |

OTHER PUBLICATIONS

Andreesen, R., "Ether Lipids in the Therapy of Cancer," *Prog. Biochem. Pharmacol.*, vol. 22, pp. 118–131 (Kaeger, Basal 1988).
Brachwitz et al, *Chemistry and Physics of Lipids*, vol. 31, pp. 33–52 (1982).
C.E. Burgos et al., *J. Org. Chem.* 52, 4973–4977 (1987).
*Cell*, vol. 15, pp. 261–267 (1978).
Greene, T.W. and Wuts, P.G., Protective Groups in Organic Synthesis, p. 68–87, J. Wiley and Sons; NY, 1991.
P.N. Guvisdalsky and R. Bittman, *J. Org. Chem.* 54, 4637–4642 (1989).
Hermetter, A. and Paltauf, F., Procedures for the Synthesis of Ether Lipids, in H.K. Mangold and F. Paltauf, *Ether Lipids*, Academic Press (1983), p. 393 et.seq.
F. Heymans et al., *Biochem. Biophys. Acta* 666, 230–237 (1981).
Janick–Buckner, D. et al., *FASEB J.* 5:320–325; 1991.
Joll, C.A.; Mortimer, B.C.; Redgrave, T.G.; Stick, R.V., *Aust. J. Chem.* 43, 1445–1448 (1990).
*J. Immunology*, vol. 119, pp. 950–954 (1977).
Kunkel, S. L., "Inflammatory Cytokines," pp. 1–15 in *Manual of Vascular Mediators*, P.A. Ward, Editor, produced by the publishers of Hospital Practice.
Nadzan, A.M., "Retinoids for the Treatment of Oncology Diseases", Chapter 13 in Annual Reports in Medicinal Chemistry–30, Academic Press Inc., 1995.
Paltauf, F. and Hermetter, A., *Methods Enzymol.*, vol. 197, pp. 134–149 (1991).
Y. Rui and D.H. Thompson, *J. Org. Chem.* 59, 5758–5762 (1994).
J.R. Surles et al., *J. Med. Chem.* 28, 73–78 (1985).
Trush et al., "The Generation of Chemiluminescence by Phagocytic Cells," *Methods in Enzymology* (1978), 57:462–494.
Yuspa, S.H. et al., *Cancer Research*, 40, 4694–4703, Dec. 1980.

*Primary Examiner*—Michael G. Ambrose
*Attorney, Agent, or Firm*—DeWitt Ross & Stevens S.C.; Salvatore R. Conte, Esq.

[57] ABSTRACT

Retinoyl substituted glycerophosphoethanolamines are disclosed having the general Formula I:

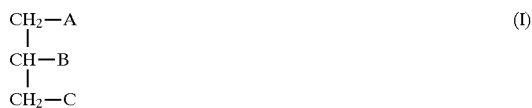

wherein one of A, B or C is a fatty ether substituent, one is a natural or synthetic retinoid ester substituent, and one is a phosphoethanolamine substituent, provided that A, B and C are each a different substituent. The optical and geometric isomers of compounds of Formula I and the pharmaceutically acceptable salts of the compounds, including the isomers, are also disclosed. The compounds (including the isomers thereof) and salts of the invention exhibit anti-tumor, anti-psoriatic and anti-inflammatory activities.

42 Claims, 2 Drawing Sheets

FIG. 1

FIG. 2

RETINOID GLYCEROL PHOSPHOLIPID CONJUGATES

Priority is claimed to provisional patent application Ser. No. 60/009,546, filed Jan. 2, 1996.

TECHNICAL FIELD

The present invention relates to certain alkyl and alkenyl glycerophosphoethanolamines substituted with a retinoid ester moiety on the glyceryl backbone, and to pharmaceutical compositions thereof. These novel compounds possess anti-psoriatic, anti-inflammatory and anti-tumor activities.

BACKGROUND OF THE INVENTION

Synthetic fatty alkyl and alkenyl ether glycerophospholipids with potential anti-tumor properties are reported in the literature, for example, see F. Paltauf and A. Hermetter, Methods in Enzymology, 197, 134–149 (1991). The particular compound, 1-O-octadecyl-2-O-methyl-sn-glycero-3-phosphocholine (ET 18-OCH$_3$), has markedly potent anti-tumor activity, see R. Andreesen, "Ether Lipids in the Therapy of Cancer", Prog. Biochem. Pharmacol., 22, 118–131 (Karger, Basel 1988). Treatment of cancer with a fatty alkyl ether glycerophosphoethanolamine component is also disclosed in U.S. Pat. No. 4,372,949. Halo substituted cytostatic analogs are described by H. Brachwitz et al., Chemistry and Physics of Lipids, 31, 33–52 (1982). Glycero-phosphoethanolamines bearing a non-cyclic $NR_1R_2$ substituent in the 2-position and a lower $C_{1-5}$ alkyl ether substituent in the 1-position are disclosed in U.S. Pat. No. 5,116,992. Applicants are unaware, however, of the hereinafter described fatty alkyl and alkenyl ether glycerophosphoethanolamines bearing a retinoyl substituent.

DESCRIPTION OF THE INVENTION

The invention relates to novel retinoyl substituted glycerophosphoethanolamines and pharmaceutical compositions thereof and also uses therefor. The subject compounds are represented by the general formula:

wherein one of A, B or C is the fatty ether substituent —O—R, one is the natural or synthetic retinoid ester (retinoyl) substituent —RET, and one is the phosphoethanolamine substituent —O—PEA, provided that A, B and C are each a different substituent. The symbols R, RET and PEA are defined hereinafter.

More particularly, the subject retinoyl substituted glycerophosphoethanolamines may be represented by the general formulas Ia, Ib and Ic (collectively the Formula I compounds):

and the enantiomeric and geometric isomers thereof, wherein: R represents a substituted or unsubstituted straight or branched chain $C_{10-24}$alkyl or alkenyl, said substituent being one or more of halo, $C_{1-3}$ alkoxy or cyano, provided that a double bond of said alkenyl does not join to the carbon atom bound to the glycero oxygen;

RET represents a retinoyl ester function; and —O—PEA represents a phosphoethanolamine of the formula:

wherein $R^1$ is hydrogen or methyl, provided that at least one $R^1$ is methyl; and PEA represents the moiety The —O—PEA moiety is also represented herein as —OPEA.

When all three of said $R^1$ are methyl, the —OPEA moiety is known as a phosphocholine moiety; with only one methyl, a phospho-(N-methyl)-ethanolamine moiety; and with two methyls, a phospho-(N,N-dimethyl)-ethanolamine moiety.

As used herein, R is $C_{10-24}$ alkyl, preferably $C_{14-20}$ alkyl and especially preferred $C_{16-18}$ alkyl, such as, for example, tetra-, penta-, hexa-hepta-, octa-, nonadecyl-, eicosyl-, or the branched analogs thereof; and R is correspondingly $C_{10-24}$ mono- (preferred) or poly-alkenyl, preferably $C_{14-20}$ alkenyl and especially preferred $C_{16-18}$ alkenyl, whereby a double bond of the alkenyl group does not join to the C atom bound to the oxygen of the glycero moiety. Both the aforementioned alkyl and alkenyl can be substituted one or more times, preferably once, with substituents which do not interfere during the synthetic steps of making the subject compounds, preferably halo, $C_{1-3}$ alkoxy or cyano. The term "halo" refers to the four halogens, chloro, bromo, iodo and fluoro, with chloro and fluoro being preferred.

The RET substituent represents the retinoyl ester function derived from a corresponding retinoic acid, natural or synthetic. It includes any geometric isomer of the carboxylate moiety (retinoyl) of retinoic acid, including the all-trans, all-cis and analogous cis-trans isomers. For example, the retinoyl ester function derived from all-trans retinoic acid has the formula:

Typical retinoyl ester functions included within the term RET designation are all-trans retinoyl, all-cis-retinoyl, 9-cis-retinoyl, 13-cis-retinoyl and the like.

The preferred compounds of Formula (I), and of preferred Formula Ia, are those wherein R is $C_{16-18}$ alkyl (most preferred) or alkenyl, RET is all-trans-retinoyl and —O—PEA is phosphocholine, for example:

1-O-octadecyl-2- (all-trans-retinoyl) -glycero-3-phosphocholine, also denoted as CPR-2003;
1-O-(9-cis-octadecenyl)-2-(all-trans-retinoyl)-glycero-3-phosphocholine; and
1-O-octahexyl-2-(all-trans-retinoyl)-glycero-3-phosphocholine.

Other particular compounds of Formula Ia are:
1-O-octadecyl-2-(all-trans-retinoyl)-glycero-3-phosphocholine-(N-methyl)-ethanolamine;
1-O-hexadecyl-2- (all-cis-retinoyl) -glycero-3-phospho-(N,N-dimethyl)-ethanolamine;
1-O-tetraeicosyl-2- (all-cis-retinoyl) -glycero-3-phosphocholine; and
1-O-(2-chloro-octadecyl)-2-(all-cis-retinoyl)-glycero-3-phosphocholine.

The preferred compounds of Formula (I), and of preferred Formula I-b, are those wherein R is $C_{16-18}$ alkyl (most preferred) or alkenyl, RET is all-trans-retinoyl and -O—PEA is phosphocholine, for example:

1-O-octadecyl-3-(all-trans-retinoyl)-glycero-2-phosphocholine, also denoted as CPR-2004;
1-O-(9-cis-octadecenyl)-3-(all-trans-retinoyl)-glycero-2-phosphocholine; and
1-O-octahexyl-3-(all-trans-retinoyl)-glycero-2-phosphocholine.

Other particular compounds of Formula Ib are:
1-O-(9-cis-octadecenyl)-3-(9-cis-retinoyl)-glycero-2-phosphocholine;
1-O-hexadecyl-3-(all-trans-retinoyl)-glycero-2-phosphocholine;
1-O-tetradecyl-3-(all-cis-retinoyl)-glycero-2-phospho-(N-methyl)-ethanolamine;
1-O-octadecyl-3-(13-cis-retinoyl)-glycero-2-phosphocholine; and
1-O-(2-methoxy-octadecyl)-3-(all-trans-retinoyl)-glycero-2-phosphocholine.

Particular compounds of Formula (Ic) are:
1-(13-cis-retinoyl)-2-O-octadecyl-glycero-3-phosphocholine;
1-(all-trans-retinoyl)-2-O-eicosyl-glycero-3-phosphocholine;
1- (all-cis-retinoyl)-2-O-decyl-glycero-3-phospho-(N-methyl)-ethanolamine;
1-(all-trans-retinoyl)-2-O-(9-cis-octadecenyl)-glycero-3-phospho-(N,N-dimethyl)-ethanolamine; and
1-(all-trans-retinoyl)-2-O-(2-cyano-octadecyl)-glycero-3-phosphocholine.

All isomeric forms of the Formula (I) compounds, including pure enantiomeric and geometric isomers and mixtures thereof, are intended to be within the scope of this invention. Unless otherwise specified, the compounds of the hereinafter examples are in racemic form.

The invention also comprehends salts of the Formula (I) compounds. These salts include acid addition salts, such as, for example, those made with hydrochloric, hydrobromic, nitric, sulfuric phosphoric, carbonic, acetic, citric or lactic acids. The salts may also include those made with bases, such as, for example, sodium hydroxide, potassium hydroxide or calcium hydroxide. The salts of the invention are made by conventional methods well known to the skilled. The salts for therapeutic use of the Formula (I) compounds are pharmaceutically acceptable salts, as understood in the art.

CHEMISTRY

The compounds of the present invention may be prepared by the stepwise procedures outlined in the following Reaction Schemes and subsequent examples. As used in the Reaction Schemes, the symbols R, PEA and RET are as previously defined. The thus-obtained compounds in the Reaction Schemes may be purified by conventional methods of the art, e.g. chromatography, recrystallization, etc.

The compounds of Formula (I) have an asymmetric carbon atom (C2 position in the glyceryl backbone) in their structure and consequently they may exist in the form of different R and S optical isomeric forms (enantiomers) or racemates. Substantially pure forms of the R-and S-isomer may be obtained, substantially free of the other, by the application of art-known resolution methodologies such as, for example, by selective crystallization or by column chromatography, or by starting their preparation from the R- or S-isomer of an appropriate precursor, for example, the starting Compound (A) shown in Reaction Scheme I.

In addition, cis-and trans-geometric isomers may also be present in the subject compounds, e.g. when R in Formula (I) is $C_{10-24}$ alkenyl, due to the cis-and trans-configuration inherent with the double bond. Thus, by initially starting with an appropriate cis-or trans-precursor, the corresponding end product of Formula I will be obtained.

All racemic and isomeric forms of the compounds of Formula (I), including pure enantiomeric and geometric isomers and mixtures thereof, are intended to be within the scope of this invention. Unless otherwise specified, the compounds of the hereinafter examples are in racemic form.

Working up the individual stepwise products indicated in the following Reaction Schemes is advantageously carried out by standard methodologies, for example, by evaporating down the reaction solution or precipitating the product from the reaction solution by dilution with appropriate antisolvents. The crude intermediate products obtained may be quite suitable, without further purification operations, for the preparation of the final products which then may be purified. Particularly suitable methods for purifying the Formula (I) compounds are the conventional chromatographic methods, such as preparative thin-layer chromatography (TLC), column chromatography, adsorption chromatography, medium pressure liquid chromatography (MPLC) or high pressure liquid chromatography (HPLC).

STARTING MATERIALS:

(C)

The compounds of formula (A) are known in the literature or are obtainable by art recognized procedures, for example, see A. Hermetter and F. Paltauf, Procedures for the Synthesis of Ether Lipids p.391–393, in H. K. Mangold and F. Paltauf, "Ether Lipids", Academic Press, 1983.

The compounds of formula (B) are also known or readily obtainable. For example, the compounds of formula (A) can be converted to formula (B) by a multistep process, requiring an hydroxyl protecting group, which is known in the literature or by art recognized procedures, for example, see F. Heymans et al, Biochem. Biophys. Acta 666, 230–237 (1981) and J. R. Surles et al, J. Med. Chem. 28, 73–78 (1985).

It has now been found that a much simpler process may be utilized. The phosphoethanolamine moiety (PEA) is introduced by the selective reaction of one of the two hydroxyl groups in compound (A) with 2-chloro-2-oxo-1,3,2-dioxaphospholane in an inert organic aprotic solvent, such as, for example, toluene (preferred), benzene, chloroform, diethyl ether, dioxane and the like, in the presence of an HCl scavenger, for example, a trialkylamine, to take up the HCl released during the reaction, followed by reaction with an appropriate $N(R^1)_3$ amine to yield the desired compound (B) and positional isomer compound (C), which are readily separated by crystallization and chromatography. This synthesis is illustrated in Example 1 hereafter.

REACTION SCHEME 1

Step 1:

Compound (B) is added to a mixture of an excess of the desired retinoic acid, dimethylaminopyridine and dicyclohexylcarbodiimide in anhydrous (ethanol-free) chloroform at room temperature. Elevated temperatures, e.g., up to 60° C., are advantageously employed to enhance the rate of the reaction in cases in which Compound (B) does not readily dissolve. After the reaction is complete, column chromatography yields the desired 2-retinoyl derivative, Compound (D).

REACTION SCHEME 2

-continued
REACTION SCHEME 2

(C)

Step 1:

The compounds of formula (E) (PG=protecting group= triphenylmethyl, trimethylsilyl;, tri-n-propylsilyl, triphenylsilyl, t-butyldimethylsilyl, t-butyldiphenylsilyl) are known in the literature or are obtainable by art recognized procedures, see T. W. Greene and P. G. Wuts, Protective Groups in Organic Synthesis, p. 68–87, J. Wiley and Sons; NY, 1991; A. Hermetter and F. Paltauf, Procedures for the Synthesis of Ether Lipids, p. 393 et.seq., in H. K. Mangold and F. Paltauf, "Ether Lipids", Academic Press, 1983; F. Paltauf and A. Hermetter, Methods Enzymol. 197, 134–149 (1991); C. E. Burgos et al, J. Org. Chem. 52, 4973–4977 (1987); P. N. Guvisdalsky and R. Bittman, J. Org. Chem. 54, 4637–4642 (1989).

The phosphoethanolamine moiety (PEA) is introduced by reaction of the hydroxyl in Compound (E) with 2-chloro-2-oxo-1,3,2-dioxaphospholane in an inert organic aprotic solvent, such as, for example, toluene (preferred), benzene, chloroform, diethyl ether, dioxane and the like, followed by reaction with an appropriate amine, $N(R^1)_3$, to yield the desired compound (F).

Step 2:

The protecting group (PG) is removed from compound (F) to yield compound (C) using methods known in the literature or by art recognizable procedures, see A. Hermetter and F. Paltauf, Procedures for the Synthesis of Ether Lipids, P. 393 et.seq., in H. K. Mangold and F. Paltauf, "Ether Lipids", Academic Press, 1983); Y. Rui and D. H. Thompson, J.Org. Chem. 59, 5758–5762 (1994); C. E. Burgos et al., J. Org. Chem. 52, 4973–4977 (1987); and F. Heymans, et al., Biochem. Biophys. Acta 666, 230–237 (1981).

REACTION SCHEME 3

Step 1:

As described in Step 1 of Reaction Scheme 1, Compound (C) is converted to Compound (G) under the same molar ratios, albeit at a higher temperature. Compound (G) is purified by chromatography.

REACTION SCHEME 4

(J) = Ic

Step 1:

The compounds of formula (H) are known in the literature or are obtainable by art recognized procedures, for example, see C. A. Joll, B. C. Mortimer, T. G. Redgrave, R. V. Stick Aust. J. Chem. 43, 1445–1448 (1990).

The phosphoethanolamine moiety (PEA) is introduced by the reaction of one of the two hydroxyl groups in Compound (H) with 2-chloro-2-oxo-1,3,2-dioxaphospholane in an inert organic aprotic solvent, such as, for example, toluene (preferred), benzene, chloroform, diethyl ether, dioxane and the like, followed by reaction with an appropriate amine, $N(R^1)3$, to yield the desired compound (I) which is purified by chromatography.

Step 2:

As described in Step 1 of Reaction Scheme 1, Compound (I) is converted to Compound (J) under the same molar ratios. Compound (J) is purified by chromatography.

UTILITY

The compounds of Formula (I), all isomeric forms thereof, and the pharmaceutically acceptable salts of the compounds and isomeric forms thereof, are useful chemopreventive and adjuvant agents in several aspects. They are useful for the treatment. of cancerous tumors and also for treating inflammation and hyperproliferative skin diseases such as psoriasis.

A. ANTI-TUMOR

The anti-tumor activity of both naturally and synthetic glycerol-derived ether lipids has been confirmed in the literature, for example, see R. Andreesen, "Ether Lipids in the Therapy of Cancer", Prog. Biochem. Pharmacol., vol.22, pp. 118–131 (Karger, Basel 1988).

The anti-tumor activity of retinoids has also been reported in the literature, for example, see A. M. Nadzan, "Retinoids for the Treatment of Oncological Diseases", Chapter 13 in Annual Reports in Medicinal Chemistry-30, Academic Press Inc., 1995.

The following testing procedure, using the human tumor cell line HL-60 in an in vitro assay, demonstrates the marked anti-tumor (or antineoplastic) activity of the subject compounds, the isomeric forms thereof, and the pharmaceutically acceptable salts of those compounds and the isomeric forms thereof. Use of the HL-60 cell line in evaluating the anti-tumor activity of retinoids is reported in the literature, for example, see Janick-Buckner, D. et al.,FASEB J. 5:320–325; 1991

Assay:

1. Human tumor cell line HL-60 (ATCC CCL 240), obtainable from the American Type Culture Collection (ATCC), a promyelocytic leukemia cell line.

2. Culture media: Roswell Park Memorial Institute-1640 (RPMI-1640) plus 10% Fetal Bovine Serum (FBS).

3. Standard protocol for culturing cell lines: in T-75 or T-150 flasks; 37° C.; 95% air, 5% $CO_2$; 100% humidity.
    a. The HL 60 cell line is passaged by removing approximately 75% of the media and cell mixture and adding an equal amount of fresh media once or twice a week.
    b. All procedures are performed aseptically in a Class II biological safety cabinet using standard BL-2 containment procedures. At approximately monthly intervals, fresh cells are thawed from liquid nitrogen storage in order to prevent genetic drift in stock cell lines.

4. Methodology:
    a. after cell passage, count cells with a hemacytometer;
    b. adjust concentration to approximately 20,000 cells per 100 $\mu$L;
    C. pipette 100 $\mu$L cell suspension per well of a standard 96-well microtiter plate;
    d. add test compound dissolved in phosphate buffered saline (PBS), or in DMSO for the comparative compound, retinoic acid, for final concentration levels ranging from 0 to 100 $\mu$M;
    e. adjust volume to 200 $\mu$L/well by adding RPMI-1640;; and
    f. incubate 72 hours under standard culture conditions and determine end points.

5. End Point 1: Cell Proliferation
    a. Add 50 $\mu$L/well of cold (4° C.) 50% (w/v) trichloroacetic acid (TCA) in water;
    b. Do not move the plate for 5 minutes;
    c. Place the plate at 4° C. for one hour;
    d. Remove TCA and rinse cells 5 times with tap water;
    e. Air-dry plates;
    f. Add 50 $\mu$L/well of 0.4% (w/v) sulforhodamine B (SRB) in 1% (v/v) acetic acid in water;
    g. After 30 minutes at room temperature, rinse cells 4 times with 1% (v/v) acetic acid in water to remove residual stain;
    h. Air-dry plates;
    i. Dissolve stain by adding 100 $\mu$L/well of unbuffered Tris base, pH 10.5;
    j. Read absorbance at 562 nm using a standard 96-well microtiter plate reader. Absorbance readings are linear with dye concentrations below 1.8 absorbance units. To reduce absorbance, decrease wavelength at which measurements are taken;
    k. Results:
       single point reading; the higher the absorbance, the higher the cell number;
       background-no cell and no test compound present in culture medium;
       control-no test compound present in culture medium;
       initial control cell number (ICCN)-no test compound present in culture medium, end point determined at the time of treatment;

final control cell number (FCCN)-no test compound present in culture medium, end point determined at 72 hours after treatment;

final cell number (FCN)-test compound present in culture medium, end point determined at 72 hours after treatment;

calculate:
ICCN=A(control, zero hour)−A(background)
FCCN=A(control, 72 hours)−A(background)
FCN=A(test compound, 72 hours)−A(background)

% Relative Increase in Cell Number=FCN−ICCN/FCCN−ICCN× 100 where A is absorbance.

Figure 1:
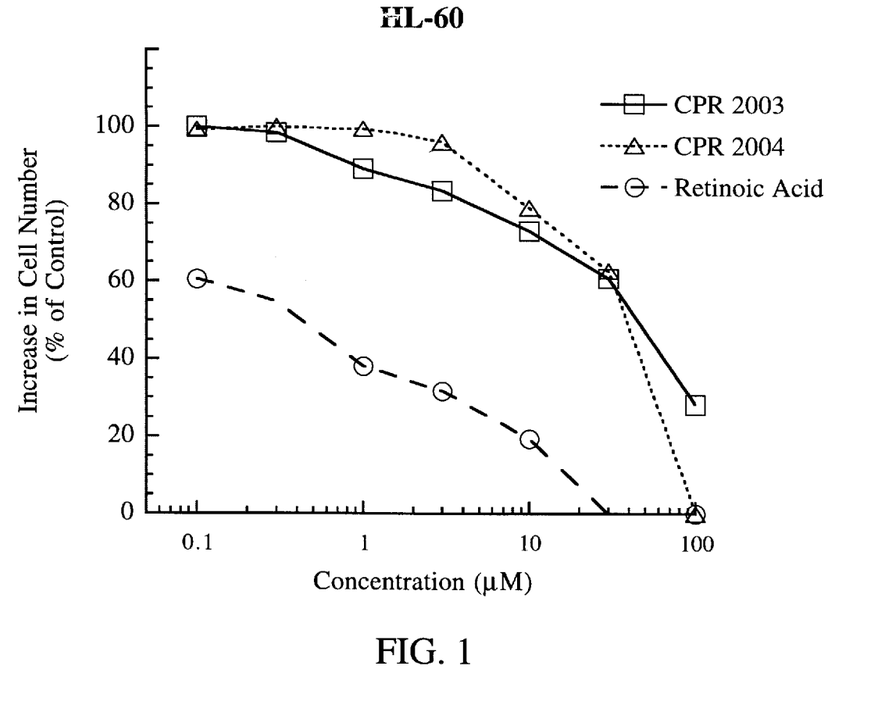
FIG. 1 is a graph representing the results from an in vitro HL-60 cell inhibition assay.

5. The results are represented in FIG. 1, which illustrates the marked cell growth inhibition by the compounds tested at concentrations above 10 $\mu$M, as compared to retinoic acid.

6. End Point 2: Cell Viability:
a. Add 100 $\mu$L/well of 0.5% (w/v) trypan blue in PBS.
b. Using a hemacytometer, determine the percent viable cells by calculating the ratio of cells that exclude trypan blue to the total number of cells.
c. The results are represented in Table 1, which illustrates the relatively high cell viability upon treatment with CPR 2003 and CPR 2004 compared to retinoic acid.

TABLE 1

| Concentration ($\mu$M) | Cell Viability HL-60 % Viability | | |
|---|---|---|---|
| | CPR 2003 | CPR 2004 | Retinoic Acid |
| 100 | 97 | 59 | 0 |
| 30 | 93 | 94 | 70 |
| 10 | 97 | 92 | 87 |

From the foregoing assay results, it is evident that the Formula (I) compounds demonstrate marked anti-tumor or anti-cancer activity, particularly against leukemia (lymphocytic, granulocytic and monocytic), as illustrated by the compounds CPR-2003 and CPR-2004.

Anti-tumor activity is to be expected against a wide spectrum of mammalian (including human) tumors and cancerous growths such as cancers of the oral cavity and pharynx (lip, tongue, mouth, pharynx), esophagus, stomach, small intestine, large intestine, rectum, liver and biliary passages, pancreas, larynx, lung, bone, connective tissue, skin, colon, breast, cervix uteri, corpus endometrium, ovary, prostate, testes, bladder, kidney and other urinary tissues, eye, brain and central nervous system, thyroid and other endocrine glands, leukemias (lymphocytic, granulacytic, monocytic), Hodgkin's disease, non-Hodgkin's lymphomas, multiple myeloma, etc. Herein the terms "tumor", "cancer" and "cancerous growths" are used synonymously.

The instant invention thus provides a method of treating a tumor in a mammal afflicted with same comprising administering to said mammal an effective anti-tumor amount of a compound of formula (I), any isomeric form thereof, or any pharmaceuticxally acceptable salt therof or any isomeric form therof. The invention also provides pharmaceutical compositions comprising an effective anti-tumor amount of a Formula (I) compound, any isomeric form thereof, or any pharmaceuticxally acceptable salt therof or any isomeric form therof, together with a pharmaceutically acceptable carrier.

B. ANTI-PSORIASIS

Psoriasis is a chronic inflammatory dermatosis characterized, in part, by hyperproliferation of keratinocytes and release of pro-inflammatory cytokines. Compounds that reduce hyperproliferation of keratinocytes in vitro are therefore likely to have utility in the control of psoriasis. As will be shown, using the assay described below with the illustrative compounds CPR 2003 and CPR 2004, the compounds of Formula (I), all of the isomeric forms thereof, and the pharmaceutically acceptable salts of those compounds and all isomeric forms thereof, markedly inhibit proliferation of these cells in vitro, thus indicating that these compounds, isomeric forms and salts are useful in ameliorating psoriasis.

Assay for Anti-psoriatic Activity by Inhibition of Keratinocyte Proliferation:

1. Cell line: PAM-212 murine keratinocyte cell line isolated and cultivated from newborn BALB/c mice (see S. H. Yuspa et al., Cancer Research, 40, 4694–4703, December, 1980) that appears to retain many characteristics of normal keratinocytes.

2. Culture medium: 1:1 DMEM and Ham's F-12 with 10% FBS.

3. Standard protocol for culturing cell lines; in T-75 or T-150 flasks; 37° C.; 95% air, 5% $CO_2$; 100% humidity. Cell line PAM-212 is passaged when approximately 80% confluent; with trypsin (1 mg/mL) and EDTA (1 mM EDTA in Ca-Mg free Hank's balanced salt solution); at a 1:4 to 1:5 split.

a. All procedures are performed aseptically in a Class II biological safety cabinet using standard BL-2 containment procedures. At approximately monthly intervals, fresh cells are thawed from liquid nitrogen storage in order to prevent genetic drift in stock cell lines.

4. Assay Procedure

After cell passage, count cells with a hemacytometer;
a. Adjust concentration to approximately 1,000 cells per 100 $\mu$L;
b. Pipette 100 $\mu$L cell suspension per well of a standard 96-well microtiter plate;
c. Preincubate 24 hours to allow cells to attach;
d. Add test compound dispersed in phosphate buffered saline (PBS), or in DMSO for the comparative compound, retinoic acid, to achieve final concentration levels ranging from 0 to 100 $\mu$M;
e. Adjust volume to 200 $\mu$L/well by adding DMEM/F12; and
f. Incubate 72 hours under standard culture conditions and determine end points.

5. End Point:

Remove media and add 100 $\mu$L/well of cold (4° C.) 10% (w/v) trichloroacetic acid (TCA) in water;
a. After 1 hour at 4° C., remove TCA and rinse cells 5 times with tap water;
b. Air-dry plates;
c. Add 50 $\mu$L/well of 0.4% (w/v) sulforhodamine B (SRB) in 1% (v/v) acetic acid in water;
d. After 30 minutes at room temperature, rinse cells 4 times with 1% (v/v) acetic acid in water to remove residual stain;
e. Air-dry plates;
f. Dissolve stain by adding 100 $\mu$L/well of unbuffered Tris base, pH 10.5;
g. Read absorbance at 562 nm using a standard 96-well microtiter plate reader. Absorbance readings are linear with dye concentrations below 1.8 absorbance units. To reduce absorbance, decrease wavelength at which measurements are taken.

6. Data Analysis:

single point reading; the higher the absorbance, the higher the cell number;
a. background-no cell and no test compound present in culture medium;
b. control-no test compound present in culture medium;
c. initial control cell number (ICCN)-no test compound present in culture medium, end point determined at the time of treatment;
d. final control cell number (FCCN)-no test compound present in culture medium, end point determined at 72 hours after treatment;
e. final cell number (FCN)-test compound present in culture medium, end point determined at 72 hours after treatment;
f. a. calculate:
ICCN=A(control, zero hour)−A(background)
FCCN=A(control, 72 hours)−A(background)
FCN=A(test compound, 72 hours)−A(background)

% Relative Increase in Cell Number=FCN−ICCN/FCCN−ICCN× 100 where A is absorbance.

Figure 2:
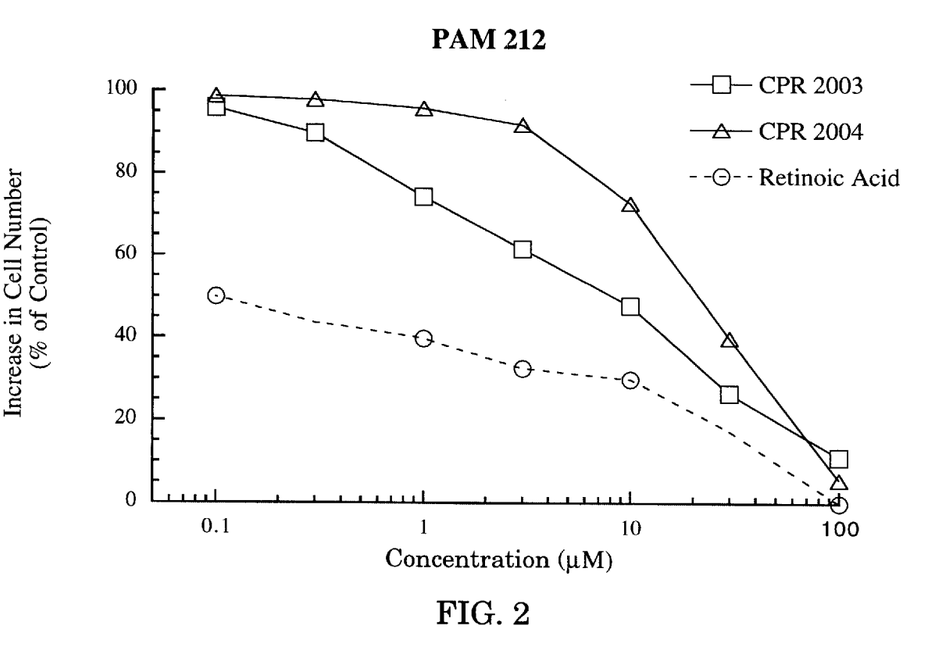
FIG. 2 is a graph representing the results from an in vitro PAM-212 cell inhibition assay.

7. Results are represented in FIG. 2, which illustrates the marked inhibition of cell growth at concentrations above 1 $\mu$M by CPR 2003 and at concentrations above 10$\mu$M by CPR 2004.

The instant invention thus provides a method of treating psoriasis in a mammal afflicted with same comprising administering to said mammal an effective anti-psoriatic amount of a compound of Formula (I), an isomeric form thereof, or a pharmaceutically acceptable salt of such a compound or isomeric form thereof. The invention thus also provides pharmaceutical compositions comprising an effective anti-psoriatic amount of a compound of Formula (I), an isomeric form thereof. or a pharmaceutically acceptable salt of such a compound or isomeric form thereof. and a pharmaceutically acceptable carrier.

C. ANTI-INFLAMMATORY

Inflammation is a complex process, involving a variety of cell types including macrophages, for example, see S. L. Kunkel, "Inflammatory Cytokines", pp. 1–15, in Manual of Vascular Mediators, P. A. Ward, Editor, produced by the publishers of Hospital Practice. References relative to macrophages are numerous, including, for example, J. Immunology 119:950–954 (1977) and Cell 15: 261–267 (1978).

Macrophages are activated by infection and by a wide variety of non-infectious irritants and proinflammatory agents. Upon activation, macrophages participate in a variety of reactions. They may phagocytize bacteria and kill them by either oxygen-dependent or -independent pathways. With respect to the oxygen-dependent pathways, activation of macrophages induces them to increase oxygen consumption and produce reactive oxygen species (for example, ozone and radicals such as superoxide). Production of reactive oxygen species by activated macrophages is associated with inflammatory responses. In addition, on activation, macrophages release a variety of inflammatory cytokines, including several interleukins and tumor necrosis factor a (TNFa). Inhibition of any of these activation-related processes can lead to reduced inflammation.

For these reasons, macrophage activation is of critical importance in studies of the inflammatory process. Agents that reduce macrophage activation are likely to have utility as anti-inflammatory agents.

As will be shown, using the assay described below with the illustrative compounds CPR 2003 and CPR 2004, the compounds of Formula (I), the isomeric forms thereof, and the pharmaceutically acceptable salt of such a compound or isomeric form thereof markedly reduce macrophage activation, thus indicating that these compounds, isomeric forms and salts are useful in ameliorating inflammation.

Assay for Anti-inflammatory Activity by Inhibition of Macrophage Chemiluminescence The RAW 264.7 cell line (available from the ATCC under accession no. TIB 71) is a murine monocyte/macrophage line the cells of which show many of the differentiative functions of a macrophage. Like macrophages, the cells are capable of phagocytosis and undergo an oxidative burst (increased oxygen consumption) and production of oxygen radicals (e.g., superoxide) in response to appropriate signals. Agents that inhibit the activation of these cells in vitro, so as to inhibit the respiratory burst and corresponding production of oxygen radicals associated with the activation, are therefore inhibitors of macrophage activation and critical steps in inflammatory processes. These agents are likely, then to be anti-inflammatories.

The respiratory burst and corresponding production of oxygen radicals that accompany macrophage activation can be measured in a variety of ways, including chemiluminescence based on the reaction of the oxygen radicals with luminol added to the culture medium (see M. A. Trush et al, 1978, "The Generation of Chemiluminescence by Phagocytic Cells." Methods in Enzymology 57: 462–494). Indeed, chemiluminescence generated from luminol in the culture medium of macrophage cell lines is recognized in the art as a marker of macrophage activation.

Cell line: RAW 264.7 (ATCC TIB 71);

1. Culture medium: DMEM with 5% FBS (attachment dependent);
2. Standard protocol for culturing cell lines: in T-75 or T-150 flasks; 37° C.; 95% air, 5% $CO_2$; 100% humidity;
3. Cell lines are passaged when approximately 80% confluent; with trypsin (1 mg/mL) and EDTA (1 mL EDTA in Ca-Mg free Hank's balanced salt solution); at a 1:4 to 1:5 split;
4. Trypsinize the cells and count with a hemacytometer;
5. Adjust concentration of cells to approximately 1,000, 000 cells per mL;
6. Suspend cells in DMEM lacking phenol red and without FBS;
7. Pipette 1 mL into a standard luminometer cuvet (12× 75), commercially obtainable from Analytical Luminescence Laboratories, San Diego;
8. Add luminol to final concentration of 1 $\mu$M;
9. Add test compound (0, 1, 3, 10, 30 $\mu$M);
10. Add 100 nanograms of phorbol myristate acetate (PMA);
11. Wait 1 minute and read photo counts (i.e., luminescence) on a Monolight 2010 luminometer available from Analytical Luminescence Laboratories;

The results are represented in Table 2, which illustrates the marked inhibition of luminescence by the compounds tested (CPR 2003 and CPR 2004) at concentrations above 3 $\mu$M. Results are calculated as percent of control (no test compound present).

TABLE 2

Inhibition of Respiratory Burst
PMA-Stimulated Mouse Macrophages

| Concentration | % Inhibition | | |
|---|---|---|---|
| (µM) | CPR 2003 | CPR 2004 | Retinoic Acid |
| 30 | 99 | 99 | 6 |
| 10 | 81 | 93 | 3 |
| 3 | 40 | 55 | 6 |
| 1 | 19 | 14 | 2 |

In view of their anti-inflammatory activity, the subject compounds are useful in the treatment of acute and chronic inflammatory diseases, such as, for example, dermatitis, conjunctivitis, bursitis, rheumatoid arthritis and the like.

The instant invention thus provides a method of treating inflammation in a mammal afflicted with same comprising administering to said mammal an effective anti-inflammatory amount of a compound of Formula (I), an isomeric form thereof, or a pharmaceutically acceptable salt of such a compound or isomeric form thereof. The invention thus also provides pharmaceutical compositions comprising an effective anti-inflammatory amount of a compound of Formula (I), an isomeric form thereof. or a pharmaceutically acceptable salt of such a compound or isomeric form thereof. and a pharmaceutically acceptable carrier.

PHARMACEUTICAL COMPOSITIONS

Pharmaceutical compositions of the present invention, comprise an active compound, i.e., a Formula (I) compound, an isomeric form thereof, or a pharmaceutically acceptable salt of the compound or isomeric form thereof, together with an acceptable carrier for it and optionally other therapeutically active ingredients. The carrier must be "pharmaceutically acceptable," i.e., be compatible with the other ingredients of the composition and not deleterious to the recipient thereof.

The compositions include those suitable for oral, rectal or parenteril (including subcutaneous, intramuscular, intradermal and intravenous) nasal, or bronchial administration. Preferred are those suitable for oral or parenteral administration. Topical formulations are also included, for example, for anti-psoriatic usage.

It is noted that the Formula (I) compounds and isomers thereof typically decompose on heating above 200° C. This characteristic may need to be taken into consideration in, for example, preparing tablets on a commercial scale where the heat of compression may be a factor. The Formula (I) compounds and isomers thereof are also rather insoluble in water and, accordingly, liquid formulations which account for this factor may be made according to art-recognized pharmaceutical techniques. Examples of these techniques include an injection wherein the active compound is dissolved in a suitable solvent or co-solvent such as an appropriate polyethylene glycol, or a propylene glycol or the like; a sealed gelatin capsule enclosing an oily solution of the active compound; a suppository of the active compound in a conventional suppository base such as cocoa butter; or a liposome formulation, for example, the active compound and a glycerophospholipid such as phosphatidylcholine. In any event, the aforementioned characteristics of the Formula (I) compounds and isomers are not uncommon in the pharmaceutical art and, accordingly, art-recognized pharmaceutical techniques are employed to prepare appropriate formulations for such compounds as those of Formula (I) and isomers or pharmaceutically acceptable salts ef either.

The formulations may conveniently be presented in unit dosage form and may be prepared by any of the methods well known in the art of pharmacy. All methods include the step of bringing the active compound or salt into association with a carrier which constitutes one or more accessory ingredients. In general, the formulations are prepared by uniformly and intimately bringing the active compound or salt into association with a liquid or solid carrier and then, if necessary, shaping the product into desired unit dosage form.

Formulations of the present invention suitable for oral administration may be presented as discrete units such as capsules, cachets, tablets, boluses or lozenges, each containing a predetermined amount of the active compound (optionally in the form of a salt thereof); as a powder or granules; or in liquid form, e.g., as suspension, solution, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

Formulations suitable for parenteral administration conveniently comprise a sterile preparation of the active compound (optionally in the form of a salt thereof) in, for example, a polyethylene glycol 200 or propylene glycol solution which is preferably isotonic with the blood of the recipient.

Useful formulations also comprise concentrated solutions or solids containing the compound of Formula (I), any isomeric form thereof, or a pharmaceutically acceptable salt of thge compound or isomeric form thereof, which upon dilution with an appropriate solvent give a solution suitable for parenteral administration.

Preparations for topical or local applications, which are, for example, conventional for anti-psoriatic usage, comprise aerosol sprays, lotions, gels, ointments, etc. and pharmaceutically acceptable vehicles therefore such as, for example, lower aliphatic alcohols, polyglycerols such as glycerol, polyethyleneglycerol, esters of fatty acids, oils and fats, silicones, and other conventional topical carriers.

In topical formulations, the compounds of Formula (I) (or isomers thereof) are preferably utilized at concentrations of from about 0.1% to about 5.0% percent by weight.

In addition to the aforementioned ingredients, the formulations of this invention may further include one or more optional accessory ingredients(s) utilized in the art of pharmaceutical formulations, e.g., diluents, buffers, flavoring agents, binders, surface active agents, thickeners, lubricants, suspending agents, preservatives (including antioxidants) and the like.

The compounds of Formula (I) (including all isomers) and salts thereof of the invention are intended to be administered under the guidance of a physician or veterinarian.

The amount of compound of Formula (I) (or any isomer thereof) or salt thereof required to be effective for each of the herein indicated activities will, of course, vary with the individual mammal being treated and is ultimately at the discretion of the medical or veterinary practitioner. The factors to be considered include the condition being treated, the route of administration, the nature of the composition, the mammal's body weight, surface area, age and general condition, and the particular compound or salt to be administered. In general, the pharmaceutical compositions of this invention contain from about 0.5 to about 500 mg and, preferably, from about 5 to about 350 mg or the active ingredient, preferably in a unit dosage form, for each of the indicated activities.

A suitable effective dose is in the range of about 0.1 to about 200 mg/kg body weight per day, preferably in the range of about 1 to about 100 mg/kg per day, calculated as the non-salt form of compound of Formula (I). The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

For example, for a 75 kg mammal (preferably an human), a dose range would be about 7.5 to about 1500 mg per day, and a typical dose would be about 800 mg per day. If discrete multiple doses are indicated, treatment might typically be 200 mg of a compound of Formula (I) given 4 times per day.

Solutions of the subject compounds of Formula (I) in PBS (phisphate-buffered saline) have characteristics indicative of the presence of liposomes. These preparations require sonication in order to form uniform, cloudy suspensions. The requirement for sonication and the cloudy appearance of the suspensions are some known properties of liposomal preparations. Additionally, foam generation, which is associated with micellar suspensions, is not a property of these preparations. Hence, unlike retinoic acid, the subject compounds are capable of forming liposomes.

The following examples are intended to illustrate and not to limit the scope of the present invention.

EXAMPLE 1

1-O-n-Octadecyl-sn-glycero-3-phosphocholine and 1-O-n-Octadecyl-sn-glycero-2-phosphocholine 4-Chloro-2-oxo-1,3,2-dioxaphospholane (33.75 g, 0.24 mol) is added in one portion to a stirred, cooled (ice-water bath) mixture of DL-batyl alcohol (DL-1-O-octadecyl-glycerol, 75 g, 0.22 mol) and triethylamine (29 mL, 0.21 mol) in anhydrous toluene under a nitrogen atmosphere. The resultant mixture is stirred while cooling with an ice-water bath for 30 minutes. The ice-water bath is removed, and the resultant mixture is allowed to warm to room temperature and then is stirred at room temperature for four days. The white solid which had precipitated is filtered off and washed with dry toluene. The toluene filtrate is concentrated in vacuo to leave a viscous residue which is further dried under high vacuum. Then, a mixture of trimethylamine (261 g) in acetonitrile (dried by distillation over phosphorus pentoxide, 2.8 L) is added to the residue. The flask which contains the residue and trimethylamine in acetonitrile is sealed by tightly connecting glass stoppers with wire and is then heated with stirring to 60°–70° C. for 24 hours. Upon cooling, a white solid precipitates. The mixture is put into a refrigerator for 24 hours to further crystallize. The mixture contains a mobile white solid and an off-white solid that is adhered to the vessel. The mobile white solid is filtered from the cold solution, and is washed sequentially with dry acetonitrile and acetone. The filtered solid is thoroughly dried under high vacuum. This white solid material is 1-O-octadecyl-glycero-3-phosphocholine free of isomeric 1-O-octadecyl-glycero-2-phosphocholine. The crystallized 1-O-octadecyl-sn-glycero-3-phosphocholine is dried under high vacuum to provide 46.46 g (41%).

The adhered solid is scraped from the vessel, ground with a mortar and pestle and dried thoroughly under high vacuum. The two titled products are separated and purified by column chromatography on silica gel. Column: 10×20 cm; the sample is applied as a solution in 70:25:5 $CHCl_3$-CH3OH-30% aqueous ammonia. The product is eluted first with 8 L of 70:25:5 and then with 10 L of 14:6:1 $CH_3OH$-$CHCl_3$-30% aqueous ammonia. Yield of pure 1-O-octadecyl-glycero-3-phosphocholine from the chromatography and after drying with high vacuum is 9.07 g (8%) [Total yield is 55.53 g (49%).] TLC (silica gel 50): 75:35:7 $CHCl_3$-$CH_3OH$-30% aqueous ammonia; Rf=0.32. The yield of pure 1-O-octadecyl-glycero-2-phosphocholine is 15.86 g (14%). TLC (silica gel 60): 75:35:7 $CHCl_3$-$CH_3OH$-30% aqueous ammonia; Rf=0.09.

EXAMPLE 2

The procedure of Example 1 is followed except that an equivalent amount of an appropriate fatty alkyl or alkenyl glycerol ether (Compound A) is substituted for the DL-batyl alcohol used therein to yield the following Compound B and Compound C respective products:

1-O-n-hexadecyl-sn-glycero-3-phosphocholine;
1-O-n-hexadecyl-sn-glycero-2-phosphocholine;
1-O-n-tetradecyl-sn-glycero-3-phosphocholine;
1-O-n-tetradecyl-sn-glycero-2-phosphocholine;
1-O-n-eicosyl-sn-glycero-3-phosphocholine;
1-O-n-eicosyl-sn-glycero-2-phosphocholine;
1-O-n-(9-cis-octadecenyl)-sn-glycero-3-phosphocholine; and
1-O-n-(9-cis-octadecenyl)-sn-glycero-2-phosphocholine.

EXAMPLE 3

1-O-n-Octadecyl-2-(all-trans-retinoyl)-glycero-3-phosphocholine (CPR-2003).

A mixture of 1-O-octadecyl-glycero-3-phosphocholine (5.00 g, 9.81 mmol, previously dried thoroughly under high vacuum), dicyclohexylcarbodiimide (5.07 g, 24.6 mmol), dimethylaminopyridine (6.01 g, 49.2 mmol), and all-trans-retinoic acid (4.31 g, 14.8 mmol) in anhydrous, ethanol free chloroform (190 mL) is stirred at room temperature under a nitrogen atmosphere. The titled product is obtained by column chromatography on silica gel; column: 5×20 cm; the crude reaction mixture is applied directly; elution with a chloroform-methanol step gradient. The product starts to elute at a chloroform:methanol ratio of 1:1. Yield of pure product is 733 mg (9.4%). TLC (silica gel 50): 70:30:7 $CHCl_3$-$CH_3OH$-30% aqueous ammonia; Rf=0.25.

EXAMPLE 4

By following the procedure of Example 3, except that an equivalent amount of the appropriate Compound B of Example 2 is utilized as the starting glycero-phospholipid, the following Compound D respective products are obtained:

1-O-n-hexadecyl-2-(all-trans-retinoyl)-glycero-3-phosphocholine;
1-O-n-tetradecyl-2-(all-trans-retinoyl)-glycero-3-phosphocholine;
1-O-n-eicosyl-2-(all-trans-retinoyl)-glycero-3-phosphocholine; and
1-O-n-(9-cis-octadecenyl)-2-(all-trans-retinoyl)-glycero-3-phosphocholine.

EXAMPLE 5

The procedure of Example 3 is followed, except that an equivalent amount of an appropriate retinoic acid analog is used in place of the all-trans retinoic acid, to yield the following Compound D respective products:

1-O-n-octadecyl-2-(all-cis-retinoyl)-glycero-3-phosphocholine;

1-O-n-octadecyl-2-(9-cis-retinoyl)-glycero-3-phosphocholine; and

1-O-n-octadecyl-2-(13-cis-retinoyl)-glycero-3-phosphocholine.

EXAMPLE 6

1-O-n-octadecyl-glycero-2-phosphocholine

Neat 4-chloro-2-oxo-1,3,2-dioxaphospholane is added over a 15 minute period to a mixture of triethylamine (9.3 g, 12.8 mL, 9 mmol), and 1-O-octadecyl-3-O-triphenylmethylglycerol (50 g,85.2 mmol) in anhydrous toluene cooled in an ice-water bath. The resultant mixture is stirred at room temperature for four days. The resultant cloudy mixture which contains a white solid precipitate is filtered. The white solid is washed thoroughly with dry toluene. The filtrate is concentrated in vacuo to a syrupy residue. The residue is further dried under high vacuum. A solution of trimethylamine (102.5 g) in acetonitrile (91.13 L, dried by distillation from phosphorus pentoxide) is added to the residue in one portion. The resultant heterogeneous mixture is heated to 70° C. for 24 hours and then cooled to 0° C. whereupon a white solid precipitated. The white solid is filtered, washed with dry acetonitrile, washed with acetone and dried under high vacuum. The product is purified by chromatography on silica gel. Column: 10×20 cm; the sample is applied as a solution in 70:25:5 $CHCl_3$-$CH_3OH$-30% aqueous ammonia. The product is eluted first with 70:25:5 and then with 14:6:1 $CH_3OH$-$CHCl_3$-30% aqueous ammonia. Yield of pure 1-O-n-octadecyl-glycero-2-phosphocholine, after drying with high vacuum, is 4.86 g (4.22%). TLC (silica gel 50): 65:35:5 $CHCl_3$-$CH_3OH$-30% aqueous ammonia; Rf=0.1.

EXAMPLE 7

By following the procedure of Example 6, the hereinafter indicated phosphoethanolamine moiety (PEA) is introduced into the appropriate fatty alkyl or alkenyl glycerol as the starting material, to yield the following Compound C respective products:

1-O-n-octadecyl-sn-glycero-2-phospho-(N-methyl)-ethanolamine;

a. 1-O-n-hexadecyl-sn-glycero-2-phospho-(N,N-dimethyl)-ethanolamine;

b. 1-O-n-hexadecyl-sn-glycero-2-phosphocholine;

c. 1-O-n-(9-cis-octadecenyl)-sn-glycero-2-phosphocholine;

d. 1-O-tetradecyl-sn-glycero-2-phospho-(N-methyl)-ethanolamine; and e. 1-O-eicosyl-sn-glycero-2-phosphocholine.

EXAMPLE 8

1-O-n-Octadecyl-3-(all-trans-retinoyl)-glycero-2-phosphocholine (CPR-2004).

A mixture of 1-O-n-Octadecyl-glycero-2-phosphocholine (1.00 g, 1.96 mmol, previously dried thoroughly under high vacuum), dicyclohexylcarbodiimide (1.15 g, 4.92 mmol), dimethylaminopyridine (1.20 g, 9.85 mmol), and all-trans-retinoic acid (0.86 g, 2.95 mmol) in anhydrous, ethanol-free chloroform (20 mL) is stirred and heated at reflux (to dissolve the reactants) under a nitrogen atmosphere. The titled product is obtained directly by column chromatography on silica gel. Column: 5×20 cm; the crude reaction mixture is applied directly; elution with a $CHCl_3$-$CHCl_3$/$CH_3OH$-$CHCl_3$/$CH_3OH$/$H_2O$ step gradient. The product starts to elute with the 10:10:1 $CHCl_3$-$CH_3OH$-$H_2O$ fraction. Yield of pure product is 378 mg (24%). TLC (silica gel 50): $CHCl_3$-$CH_3OH$-30% aqueous ammonia 70:30:7; Rf=0.25.

EXAMPLE 9

By following the procedure of Example 8, except that an equivalent amount of the appropriate Compound C, and an equivalent amount of the appropriate retinoic acid, are utilized as the starting materials, the following Compound G respective products are obtained:

1-O-n-octadecyl-3-(all-cis-retinoyl)-glycero-2-phosphocholine;

1-O-n-hexadecyl-3-(all-trans-retinoyl)-glycero-2-phosphocholine;

1-O-n-hexadecyl-3-(all-cis-retinoyl)-glycero-2-phosphocholine;

1-O-n-tetradecyl-3-(all-cis-retinoyl)-glycero-2-phospho-(N-methyl)-ethanolamine;

1-O-(9-cis-octadecenyl)-3-(9-cis-retinoyl)-glycero-2-phosphocholine; and

1-O-eicosyl-3-(13-cis-retinoyl)-glycero-2-phospho-(N,N-dimethyl)-ethanolamine.

EXAMPLE 10

2-O-n-Octadecyl-sn-glycero-1-phosphocholine

4-Chloro-2-oxo-1,3,2-dioxaphospholane (33.75 g, 0.24 mol) is added in one portion to a stirred, cooled (ice-water bath) mixture of B-batyl alcohol (DL-2-O-octadecyl-glycerol, 45 g, 0.13 mol) and triethylamine (17.5 mL, 0.13 mol) in anhydrous toluene under a nitrogen atmosphere. The resultant mixture is stirred while cooling with an ice-water bath for 30 minutes. The ice-water bath is removed, and the resultant mixture is allowed to warm to room temperature and then is stirred at room temperature for four days. The white solid which had precipitated is filtered off and washed with dry toluene. The toluene filtrate is concentrated in vacuo to leave a viscous residue which is further dried under high vacuum. Then, a mixture of trimethylamine (157 g) in acetonitrile (dried by distillation over phosphorus pentoxide, 1.7 L) is added to the residue. The flask which contains the residue and trimethylamine in acetonitrile is sealed by tightly connecting glass stoppers with wire and is then heated with stirring to 60°–70° C. for 24 hours. Upon cooling, a white solid precipitates. The mixture is put into a refrigerator for 24 hours to further crystallize. The white solid precipitate is filtered from the cold solution, and is washed sequentially with dry acetonitrile and acetone. The filtered solid is thoroughly dried under high vacuum. The solid is ground with a mortar and pestle and dried thoroughly under high vacuum. The crude 2-O-n-Octadecyl-glycero-1-phosphocholine is purified by column chromatography on silica gel.

EXAMPLE 11

2-O-n-Octadecyl-1-(all-trans-retinoyl)-glycero-3-phosphocholine

A mixture of 1-O-n-Octadecyl-glycero-2-phosphocholine (5.0 g, 2.55 mmol, previously dried thoroughly under high vacuum), dicyclohexylcarbodiimide (5.75 g, 24.6 mmol), dimethylaminopyridine (6.0 g, 49.2 mmol), and all-trans-retinoic acid (4.3 g, 14.7 mmol) in anhydrous, ethanol-free chloroform (100 mL) is stirred and heated at reflux (to dissolve the reactants) under a nitrogen atmosphere. The product is obtained directly by column chromatography on silica gel. Column: 10×20 cm; the crude reaction mixture is applied directly. Elution with a chloroform-methanol step gradient (2 L CHCl$_3$, 6L 19:1, 3L 9:1, 4.5 L 6:1, 8L 7:3, 15L 6:4, 25L 10:10:1 CHCl$_3$-CH$_3$OH-H$_2$O). The product starts to elute with 10:10:1 CHCl$_3$-CH$_3$OH-H$_2$O fraction. Yield of pure product is 2.44 g (31%). TLC (silica gel 50): CHCl$_3$-CH$_3$OH-30% aqueous ammonia 70:30:7; Rf=0.26.

EXAMPLE 12

The procedure of Example 11 is followed, except that an equivalent amount of an appropriate retinoic acid is utilized, to yield the following respective products:

2-O-n-octadecyl-1-(all-cis-retinoyl)-glycero-3-phosphocholine;

2-O-n-octadecyl-1-(13-cis-retinoyl)-glycero-3-phosphocholine; and

2-O-n-octadecyl-1-(9-cis-retinoyl)-glycero-3-phosphocholine.

EXAMPLE 13

The following are illustrative examples of pharmaceutical compositions containing the indicated ingredients which may be prepared in conventional methodologies of the art.

| A. Tablets | |
|---|---|
| Ingredient | Per Tablet (mg) |
| CPR-2003 | 50–100 |
| Lactose | 70 |
| Maize starch | 70 |
| Polyvinylpyrrolidone | 5 |
| Magnesium stearate | 5 |
| Tablet weight | 200–250 |
| B. Oil-in-Water Cream Base Formulation: | |
| Ingredient | Weight (g) |
| CPR-2003 | 10.0 |
| Anhydrous lanolin | 20.0 |
| Polysorbate 60 | 4.0 |
| Sorbitan monopalmitate | 2.0 |
| Light liquid paraffin | 4.0 |
| Propylene glycol | 5.0 |
| Methyl hydroxybenzoate | 0.1 |
| Purified water | to 100.0 |
| C. Capsules: | |
| Ingredient | Per Capsule (mg) |
| CPR 2004 | 50 |
| Lactose | 450 |
| Magnesium stearate | 5 |
| Capsule weight | 505 |
| D. Injection-for 1000 ampules: | |
| Ingredient | Amount |
| Active compound | 5 g |
| Buffering agents | q.s. |
| Propylene glycol | 400 mg |
| Water for injection | 600 ml |

The active compound and buffering agents are dissolved in the propylene glycol at about 50° C. The water for injection is then added with stirring and the resulting solution is filtered, filled into ampules, sealed and sterilized by autoclaving.

What is claimed is:

1. Retinoyl substituted glycerophosphoethanolamines of the general Formulas Ia, Ib and Ic:

Ia

Ib

Ic all geometric and optical isomers thereof, and the pharmaceutically acceptable salts of said compounds and isomers, wherein:

R represents a substituted or unsubstituted straight or branched chain C$_{10\text{-}24}$ alkyl, any such substituent being one or more of halo, C$_{1\text{-}3}$ alkoxy or cyano;

RET represents a retinoyl ester moiety; and

-OPEA represents a phosphoethanolamine moiety of the formula:

wherein R$^1$ is hydrogen or methyl, provided that at least one R$^1$ is methyl.

2. A glycerophosphoethanolamine of claim 1 wherein said RET is selected from the group consisting of all-trans-, all-cis-, 9-cis- and 13-cis- retinoyl.

3. A glycerophosphoethanolamine of claim 2 wherein said RET is all-trans-retinoyl.

4. A glycerophosphoethanolamine of claim 1, which is of Formula Ia or Formula Ib, or any optical or geometric isomer thereof or pharmaceutically acceptable salt of said compound or isomer, wherein said RET is selected from the group consisting of all-trans-, all-cis-, 9-cis- and 13-cis-retinoyl.

5. A glycerophosphoethanolamine of claim 4 wherein RET is all-trans-retinoyl.

6. A glycerophosphoethanolamine of claim 1 wherein R is C$_{14\text{-}20}$ alkyl.

7. A glycerophosphoethanolamine of claim 6 wherein R is C$_{16\text{-}18}$ alkyl.

8. A glycerophosphoethanolamine of claim 1 which is of Formula Ia or Ib and wherein RET is all-trans-retinoyl, R is C$_{16\text{-}18}$ alkyl, and R$^1$ is methyl.

9. A compound of claim 1 which is selected from the group consisting of the optical isomers of 1-O-octadecyl-2-(all-trans-retinoyl)-glycero-3-phosphocholine and the optical isomers of 1-O-n-Octadecyl-3-(all-trans-retinoyl)-glycero-2-phosphocholine.

10. A mixture of compounds, which mixture is selected from the group consisting of a racemic mixture of the optical isomers of 1-O-octadecyl-2-(all-trans-retinoyl)-glycero-3-phosphocholine and a racemic mixture of the optical isomers of 1-O-n-Octadecyl-3-(all-trans-retinoyl)-glycero-2-phosphocholine.

11. A method of treating a solid neoplastic tumor or a leukemia in a mammal afflicted with same comprising administering to said mammal an anti-tumor effective or anti-leukemia effective amount of a glycerophosphoethanolamine of Formula Ia, Ib, or Ic:

or any geometric or optical isomer of any of them, or any pharmaceutically acceptable salt of any of said compounds or isomers thereof, wherein:

R represents a substituted or unsubstituted straight or branched chain $C_{10-24}$ alkyl, said substituent being one or more of halo, $C_{1-3}$ alkoxy or cyano;

RET represents a retinoyl ester function; and

-OPEA represent a phosphoethanolamine of the formula:

wherein $R^1$ is hydrogen or methyl, provided that at least one $R^1$ is methyl.

12. The method of claim 11 wherein said glycerophosphoethanolamine is a compound of Formula Ia or Formula Ib, and RET is selected from the group consisting of all-trans-, all-cis-, 9-cis- and 13-cis-retinoyl.

13. The method of claim 12 wherein said glycerophosphoethanolamine is a compound of said Formula Ia or Formula Ib wherein RET is all-trans-retinoyl, R is $C_{16-18}$ alkyl, and $R^1$ is methyl.

14. The method of claim 13 wherein said glycerophosphoethanolamine is selected from the group consisting of:
1-O-octadecyl-2-(all-trans-retinoyl)-glycero-3-phosphocholine; and
1-O-n-Octadecyl-3-(all-trans-retinoyl)-glycero-2-phosphocholine.

15. The method of claim 14 wherein what is administered to the mammal is a compound selected from the group consisting of the optical isomers of 1-O-octadecyl-2-(all-trans-retinoyl)-glycero-3-phosphocholine and the optical isomers of 1-O-n-Octadecyl-3-(all-trans-retinoyl)-glycero-2-phosphocholine.

16. The method of claim 15 wherein what is administered to the mammal is a mixture of compounds, which mixture is selected from the group consisting of a racemic mixture of the optical isomers of 1-O-octadecyl-2-(all-trans-retinoyl)-glycero-3-phosphocholine and a racemic mixture of the optical isomers of 1-O-n-octadecyl-3-(all-trans-retinoyl)-glycero-2-phosphocholine.

17. The method of any of claims 11–16 wherein the mammal being treated is an human.

18. A method of treating psoriasis in a mammal suffering therefrom comprising administering to said human an anti-psoriatic effective amount of a glycerophosphoethanolamine of Formula Ia, Ib or Ic:

or any geometric or optical isomer of any of them, or any pharmaceutically acceptable salt of any of said compounds or isomers thereof, wherein:

R represents a substituted or unsubstituted straight or branched chain $C_{10-24}$ alkyl, said substituent being one or more of halo, $C_{1-3}$ alkoxy or cyano;

RET represents a retinoyl ester function; and

-OPEA represents a phosphoethanolamine of the formula:

wherein $R^1$ is hydrogen or methyl, provided that at least one $R^1$ is methyl.

19. The method of claim 18 wherein said glycerophosphoethanolamine is a compound of Formula Ia or Formula Ib, and RET is selected from the group consisting of all-trans-, all-cis-, 9-cis- and 13-cis-retinoyl.

20. The method of claim 19 wherein said glycerophosphoethanolamine is a compound of said Formula Ia or Formula Ib wherein RET is all-trans-retinoyl, R is $C_{16-18}$ alkyl, and $R^1$ is methyl.

21. The method of claim 20 wherein said glycerophosphoethanolamine is selected from the group consisting of:
1-0-octadecyl-2-(all-trans-retinoyl)-glycero-3-phosphocholine; and
1-0-n-Octadecyl-3-(all-trans-retinoyl)-glycero-2-phosphocholine.

22. The method of claim 21 wherein what is administered to the human is a compound selected from the group consisting of the optical isomers of 1-O-octadecyl-2-(all-trans-retinoyl)-glycero-3-phosphocholine and the optical isomers of 1-O-n-octadecyl-3 -(all-trans-retinoyl)-glycero-2 -phosphocholine.

23. The method of claim 22 wherein what is administered to the human is a mixture of compounds, which mixture is selected from the group consisting of a racemic mixture of the optical isomers of 1-O-octadecyl-2-(all-trans-retinoyl)-glycero-3-phosphocholine and a racemic mixture of the optical isomers of 1-O-n-Octadecyl-3-(all-trans-retinoyl)-glycero-2-phosphocholine.

24. A method of treating inflammation in a mammal suffering therefrom comprising administering to said mammal an anti-inflammation effective amount of a glycerophosphoethanolamine of Formula Ia, Ib or Ic:

$$\begin{bmatrix} -O-R \\ -RET \\ -O-PEA \end{bmatrix} \quad Ia$$

$$\begin{bmatrix} -O-R \\ -O-PEA \\ -RET \end{bmatrix} \quad Ib$$

$$\begin{bmatrix} -RET \\ -O-R \\ -O-PEA \end{bmatrix} \quad Ic$$

or any geometric or optical isomer of any of them, or any pharmaceutically acceptable salt of any of said compounds or isomers thereof, wherein:

R represents a substituted or unsubstituted straight or branched chain $C_{10\text{-}24}$ alkyl, said substituent being one or more of halo, $C_{1\text{-}3}$ alkoxy or cyano;

RET represents a retinoyl ester function; and

-OPEA represents a phosphoethanolamine of the formula:

$$-O-\underset{\underset{O^-}{|}}{\overset{\overset{O}{\|}}{P}}-O-(CH_2)_2-N^+(R^1)_3$$

wherein $R^1$ is hydrogen or methyl, provided that at least one $R^1$ is methyl.

25. The method of claim 24 wherein said glycerophosphoethanolamine is a compound of Formula Ia or Formula Ib, and RET is selected from the group consisting of all-trans-, all-cis-, 9-cis- and 13-cis-retinoyl.

26. The method of claim 25 wherein said glycerophosphoethanolamine is a compound of said Formula Ia or Formula Ib wherein RET is all-trans-retinoyl, R is $C_{16\text{-}18}$ alkyl, and $R^1$ is methyl.

27. The method of claim 26 wherein said glycerophosphoethanolamine is selected from the group consisting of:
1-O-octadecyl-2-(all-trans-retinoyl)-glycero-3-phosphocholine; and
1-O-n-Octadecyl-3-(all-trans-retinoyl)-glycero-2-phosphocholine.

28. The method of claim 27 wherein what is administered to the mammal is a compound selected from the group consisting of the optical isomers of 1-O-octadecyl-2-(all-trans-retinoyl)-glycero-3-phosphocholine and the optical isomers of 1-O-n-octadecyl-3 -(all-trans-retinoyl)-glycero-2-phosphocholine.

29. The method of claim 28 wherein what is administered to the mammal is a mixture of compounds, which mixture is selected from the group consisting of a racemic mixture of the optical isomers of 1-O-octadecyl-2-(all-trans-retinoyl)-glycero-3-phosphocholine and a racemic mixture of the optical isomers of 1-O-n-Octadecyl-3-(all-trans-retinoyl)-glycero-2-phosphocholine.

30. The method of any of claims 24–29 wherein the mammal being treated is an human.

31. A pharmaceutical composition comprising (i) an anti-tumor-, anti-psoriatic- or anti-inflammatory-effective amount of a retinoyl substituted glycerophosphoethanolamine of the general Formula Ia, Ib or Ic:

$$\begin{bmatrix} -O-R \\ -RET \\ -O-PEA \end{bmatrix} \quad Ia$$

$$\begin{bmatrix} -O-R \\ -O-PEA \\ -RET \end{bmatrix} \quad Ib$$

$$\begin{bmatrix} -RET \\ -O-R \\ -O-PEA \end{bmatrix} \quad Ic$$

or any geometric or optical isomer of any of them, or any pharmaceutically acceptable salt of any of said compounds or isomers thereof, wherein:

R represents a substituted or unsubstituted straight or branched chain $C_{10\text{-}24}$ alkyl, said substituent being one or more of halo, $C_{1\text{-}3}$ alkoxy or cyano;

RET represents a retinoyl ester function; and

-OPEA represents a phosphoethanolamine of the formula:

$$-O-\underset{\underset{O^-}{|}}{\overset{\overset{O}{\|}}{P}}-O-(CH_2)_2-N^+(R^1)_3$$

wherein $R^1$ is hydrogen or methyl, provided that at least one $R^1$ is methyl; and (ii) a pharmaceutically effective carrier.

32. The composition of claim 31 wherein said RET is selected from the group consisting of all-trans-, all-cis-, 9-cis- and 13-cis- retinoyl.

33. The composition of claim 32 wherein said glycerophosphoethanolamine is a Formula Ia or Formula Ib compound and said RET is all-trans-retinoyl.

34. The composition of claim 33 wherein said R is $C_{14\text{-}20}$ alkyl.

35. The composition of claim 34 wherein said R is $C_{16\text{-}18}$ alkyl.

36. The composition of claim 35 wherein said said $R^1$ is methyl.

37. The composition of claim 36 wherein said glycerophosphoethanolamine is selected from the group consisting of:
1-O-octadecyl-2-(all-trans-retinoyl)-glycero-3-phosphocholine; and
1-O-n-Octadecyl-3-(all-trans-retinoyl)-glycero-2-phosphocholine.

38. The composition of claim 37 wherein said glycerophosphoethanolamine is a compound selected from the group consisting of the optical isomers of 1-O-octadecyl-2-(all-trans-retinoyl)-glycero-3-phosphocholine and the optical isomers of 1-O-n-octadecyl-3-(all-trans-retinoyl)-glycero-2-phosphocholine.

39. The composition of claim 38 wherein there is a mixture of glycerophosphoethanolamines, said mixture selected from the group consisting of a racemic mixture of the optical isomers of 1-O-octadecyl-2-(all-trans-retinoyl)-glycero-3-phosphocholine and a racemic mixture of the optical isomers of 1-O-n-Octadecyl-3-(all-trans-retinoyl)-glycero-2-phosphocholine.

40. A pharmaceutical composition for topical use comprising from about 0.1 to about 5.0 weight percent of a compound of claim 1 and a pharmaceutically acceptable carrier in ointment form.

41. The composition of claim 40 wherein said compound is a Formula Ia or Formula Ib compound wherein RET is all-trans-retinoyl, R is $C_{16-18}$ alkyl and $R^1$ is methyl.

42. The topical composition of claim 41 wherein said compound is:

1-O-octadecyl-2-(all-trans-retinoyl)-glycero-3-phosphocholine; or

1-O-octadecyl-3-(all-trans-retinoyl)-glycero-2-phosphocholine.

* * * * *